United States Patent
Oestreich et al.

(10) Patent No.: US 9,518,070 B2
(45) Date of Patent: Dec. 13, 2016

(54) USE OF CYCLOHEXA-2,5-DIEN-1-YL-SILANES AS PRECURSORS FOR GASEOUS HYDROSILANES

(71) Applicant: TECHNISCHE UNIVERSITÄT BERLIN, Berlin (DE)

(72) Inventors: Martin Oestreich, Berlin (DE); Antoine Simonneau, Toulouse (DE)

(73) Assignee: TECHNISCHE UNIVERSITAET BERLIN, Berlin (DE)

( * ) Notice: Subject to any disclaimer, the term of this patent is extended or adjusted under 35 U.S.C. 154(b) by 0 days.

(21) Appl. No.: 15/021,222

(22) PCT Filed: Sep. 4, 2014

(86) PCT No.: PCT/EP2014/068798
§ 371 (c)(1),
(2) Date: Mar. 10, 2016

(87) PCT Pub. No.: WO2015/036309
PCT Pub. Date: Mar. 19, 2015

(65) Prior Publication Data
US 2016/0222037 A1 Aug. 4, 2016

(30) Foreign Application Priority Data
Sep. 10, 2013 (EP) .................. 13183727
May 15, 2014 (EP) .................. 14168521

(51) Int. Cl.
*C07F 7/06* (2006.01)
*C07F 7/08* (2006.01)
*C07B 63/02* (2006.01)

(52) U.S. Cl.
CPC ............. *C07F 7/0827* (2013.01); *C07B 63/02* (2013.01); *C07F 7/083* (2013.01); *C07F 7/0809* (2013.01)

(58) Field of Classification Search
CPC ...................................... C07F 7/08
USPC ...................................... 556/481
See application file for complete search history.

(56) References Cited

U.S. PATENT DOCUMENTS
2007/0142632 A1 6/2007 Gouverneur

FOREIGN PATENT DOCUMENTS
DE 10326577 5/2004

OTHER PUBLICATIONS

Rendler Sebastian; Oestreich Martin; Angewandte Chemie—International Edition (Jul. 28, 2008), vol. 47, No. 32, pp. 5997-6000.*
Rendler et al. Angew. Chem. Int. Ed. 2008, English Translation, vol. 47, pp. 5997-6000, Original vol. 120, pp. 6086-6089, English Translation and original all together 8 Pages, "Conclusive Evidence for an SN2—Si Mechanism in the B(C6F5)3-Catalyzed Hydrosilylation of Carbonyl Compounds: Implications for the Related Hydrogenation".
International Search Report for PCT/EP2014/068798, Completed by the European Patent Office on Oct. 21, 2014, 5 Pages.
Simonneau et al. Angew. Chem. Int. Ed. 2013, vol. 52, pp. 11905-11907, "3-Silylated Cyclohexa-1,4-dienes as Precursors for Gaseous Hydrosilanes: The B(C6F5)3-Catalyzed Transfer Hydrosilylation of Alkenes".
Amrein et al. Organic Letters 2001, vol. 3, No. 15, pp. 2357-2360, "Radical Transfer Hydrosilylation/ Cyclization Using Silylated Cyclohexadienes".
Landais et al. Eur. J. Org. Chem. 2002, pp. 4037-4053, "Desymmetrization of Cyclohexa-1,4-dienes—A Straightforward Route to Cyclic and Acyclic Polyhydroxylated Systems".
Angelaud et al. J. Org. Chem. 1999, vol. 64, pp. 9613-9624, "Desymmetrization of Cyclohexadienylsilanes. Regio-, Diastereo-, and Enantioselective Access to Sugar Mimics".
Ishikawa et al. Journal of Organometallic Chemistry 1976, vol. 118, pp. 155-160, "Photochemically Generated Silicon-Carbon Double-Bonded Intermediates, The Reaction of p-Tolylpentamethyldisilane with Methanol and Methanol-d".
Eaborn et al. Journal of the Chemical Society Jan. 1, 1974, pp. 2055-2061, "Reduction of Aryltrimethylsilanes as a Synthetic Method. Part I. Electrochemical Reduction".

* cited by examiner

*Primary Examiner* — Porfirio Nazario Gonzalez
*Assistant Examiner* — Kofi Adzamli
(74) *Attorney, Agent, or Firm* — Brooks Kushman P.C.

(57) ABSTRACT

A method of making hydrosilanes having a formula $R^1R^2R^3SiH$ by reacting a compound having formula I:

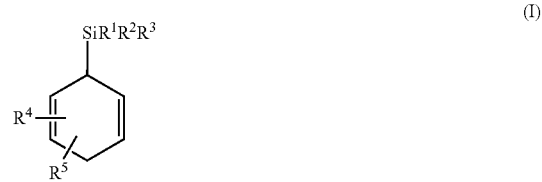

(I)

in solution using a strong Lewis acid. This way, e.g., alkenes or carbonyl compounds can be hydrosilylated in good yields using the cyclohexa-2,5-dien-1-yl-silanes of general formula I as transfer hydrosilylating agents in the presence of a strong Lewis acid as catalyst with concomitant formation of an arene solvent.

14 Claims, No Drawings

USE OF CYCLOHEXA-2,5-DIEN-1-YL-SILANES AS PRECURSORS FOR GASEOUS HYDROSILANES

CROSS-REFERENCE TO RELATED APPLICATION

This application is the U.S. national phase of PCT Application No. PCT/EP2014/068798 filed on Sep. 4, 2014, which claims priority to EP Patent Application No. 13183727.0 filed on Sep. 10, 2013, and EP Patent Application No. 14168521.4 filed May 15, 2014 the disclosures of which are incorporated in their entirety by reference herein.

The invention relates to the use of cyclohexa-2,5-dien-1-yl-silanes of general formula I to generate hydrosilanes in solution using a strong Lewis acid. This way e.g. alkenes or carbonyl compounds can be hydrosilylated in good yields using the cyclohexa-2,5-dien-1-yl-silanes of general formula I as transfer hydrosilylating agents in the presence of a strong Lewis acid as catalyst with concomitant formation of an arene solvent.

Alkene hydrosilylation is one of the prevalent methods for carbon-silicon bond formation in academic as well as in industrial settings. Usually catalyzed by precious late transition metal complexes, substantial progress is currently being made in the design of catalysts based on more abundant transition metals. Various triorganosilanes ($R_3SiH$) but also flammable trichlorosilane ($Cl_3SiH$) and harmful trialkoxysilanes [$(RO)_3SiH$ with R=Me or Et] are commonly employed in these catalyses. Conversely, $Me_3SiH$ and $Me_2SiH_2$ are rarely applied as handling of these highly flammable and potentially explosive gases is inconvenient from a safety point of view.

Practical methods avoiding these issues would, therefore, be relevant to several areas of silicon chemistry and are the object of the present invention.

The inventors of the present invention have solved this problem by using cyclohexa-2,5-dien-1-yl-silanes of general formula I

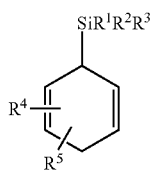 (I)

wherein
$R^1$ and $R^2$ represent independently from each other $C_1$-$C_3$-alkyl or $C_1$-$C_3$-alkoxy,
$R^3$ represent independently from $R^1$ and $R^2$ H, $C_1$-$C_3$-alkyl, $C_1$-$C_3$-alkoxy or aryl and
$R^4$ and $R^5$ represent independently from each other H, $C_1$-$C_3$-alkyl or $R^1R^2R^3Si$ with
$R^1$ to $R^3$ as defined above,
for generation of hydrosilanes of general formula Ia in solution

 (Ia), with $R^1$ to $R^3$ as above,
using a Lewis acid of general formulae II or IIa

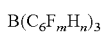 (II)

wherein m+n=5, m=0 to 5 and n=0 to 5,

 (IIa)

wherein R is methyl or ethyl,
under concomitant formation of an arene solvent.

The inventors have found that cyclohexa-2,5-dien-1-yl-silanes of general formula I serve as viable hydrosilane precursors. It revealed that Lewis acids, particularly the Lewis acids of formulae II and IIa, a few of them being commercially available, were able to catalyze the release of hydrosilanes of formula Ia from cyclohexa-2,5-dien-1-yl-silanes of formula I.

This new technique was used for hydrosilylation of alkenes and carbonyl compounds which was promoted by the same catalysts of formula II and IIa. It was found that the alkenes of general formula III

 (III)

react in solution with the formed hydrosilanes of general formula Ia

 (Ia), wherein $R^1$ to $R^3$ have the above meaning,
to silanes of general formula IV

 (IV)

with $R^1$ to $R^3$ as above.

In the same way carbonyl compounds of general formula V

 (V)

react in solution with the formed hydrosilanes of general formula Ia

 (Ia), wherein $R^1$ to $R^3$ have the above meaning,
to form silanes of general formula VI

 (VI)

with $R^1$ to $R^3$ as above.

Therefore, the net reaction corresponds to an unprecedented ionic transfer hydrosilylation of alkenes or carbonyl compounds using cyclohexa-2,5-dien-1-yl-silanes of general formula I catalyzed by the Lewis acids of formula II or IIa under concomitant formation of an arene solvent. The byproducts of this reaction, arene solvent and unreacted hydrosilane of formula Ia, can be easily removed from the reaction mixture. Accordingly, the hydrosilylation of alkenes and carbonyl compounds is also an object of the present invention.

According to the present invention $C_1$-$C_3$-alkyl means methyl, ethyl, n-propyl or i-propyl and $C_1$-$C_3$-alkoxy means methoxy, ethoxy, 1-propoxy or 2-propoxy. Aryl means substituted or unsubstituted aryl, preferably substituted or unsubstituted phenyl, tolyl, xylyl, mesityl, naphth-1-yl and naphth-2-yl. Arene solvents according to the invention are benzene, alkyl or triorganosilyl benzenes, preferably toluene, xylene cumene or trimethylsilyl benzene.

In an embodiment of the invention, cyclohexa-2,5-dien-1-yl-silanes of general formula I are used wherein $R^1$, $R^2$ and $R^3$ are equal to each other representing methyl, ethyl, i-propyl, methoxy or ethoxy. In a preferred embodiment of the invention, $R^1$, $R^2$ and $R^3$ are methyl, ethyl, methoxy or ethoxy. It is especially preferred that $R^1$, $R^2$ and $R^3$ are methyl, methoxy or ethoxy.

In another embodiment of he invention at least one of $R^4$ and $R^5$ in formula I is methyl or trimethylsilyl.

In yet another embodiment of the invention cyclohexa-2,5-dien-1-yl-silanes of general formula I are used wherein $R^1$ and $R^2$ are equal to each other representing methyl, ethyl, methoxy or ethoxy, preferably methyl and methoxy, and $R^3$ represents H or aryl, preferably phenyl.

Following compounds of formula I are particularly preferred:

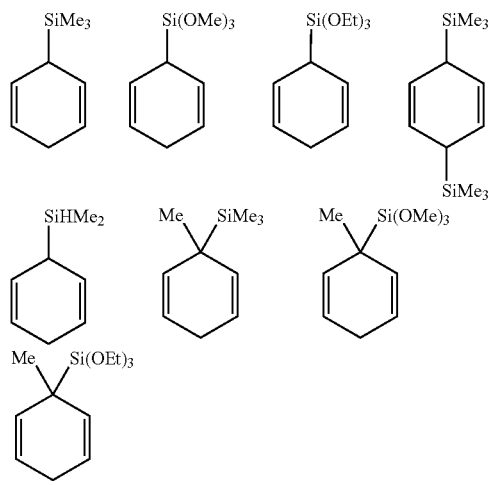

According to the invention, in one embodiment the catalyst of formula II is tris(pentafluorophenyl)borane $B(C_6F_3)_3$, but also boron trifluoride diethyletherate or dimethyletherate of formula II can be used, preferably boron trifluoride diethyletherate. It is also possible to use $AlCl_3$ as catalyst.

The release of hydrosilanes from formula I and the hydrosilylation of alkenes are conducted in a solvent at ambient temperature. According to the present invention, ambient temperature means 15 to 30° C. The hydrosilylation of carbonyl compounds is conducted at 70-120° C. As solvent it is preferred to use an arene solvent, preferably benzene, toluene, xylene, or a halogenated solvent, preferably $CH_2Cl_2$, 1,2-clichlorethane or chloroform. Transfer hydrosilylation of alkenes occurred in high yields from 80 to 95% in $CH_2Cl_2$ with cyclohexa-2,5-dien-1-yl-trimethylsilane of formula I as precursor. It is remarkable that only little excess of this precursor is necessary for high yield, because this precursor is gaseous at room temperature.

Transfer hydrosilylation of carbonyl compounds occurred in high yields fro 90-99% in benzene with cyclohexa-2,5-dien-1-yl-trimethylsilane of formula I as precursor.

According to one embodiment of the present invention the alkenes which are hydrosilylated are alkenes of general formula IIIa

wherein
$R^6$ represents H, $C_4$-$C_{20}$-alkyl, $C_4$-$C_{20}$-cycloalkyl or aryl, preferably $C_4$-$C_6$-alkyl or phenyl,
$R^7$ represents H, $C_1$-$C_{10}$-alkyl, $C_4$-$C_{10}$-cycloalkyl or aryl, preferably $C_1$-$C_4$-alkyl or phenyl,
or $R^6$ and $R^7$ form together a cycloalkane ring, preferably a cyclohexane ring, and
$R^8$ represents H, methyl, ethyl, —$CH_2$Hal or phenyl.

According to the present invention Hal means halogen being chlorine, bromine or iodine, preferably chlorine or bromine.

Some alkenes of formula IIIa which are hydrosilylated with cyclohexa-2,5-dien-1-yl-trimethylsilane of formula I and their end products are given in Table 1:

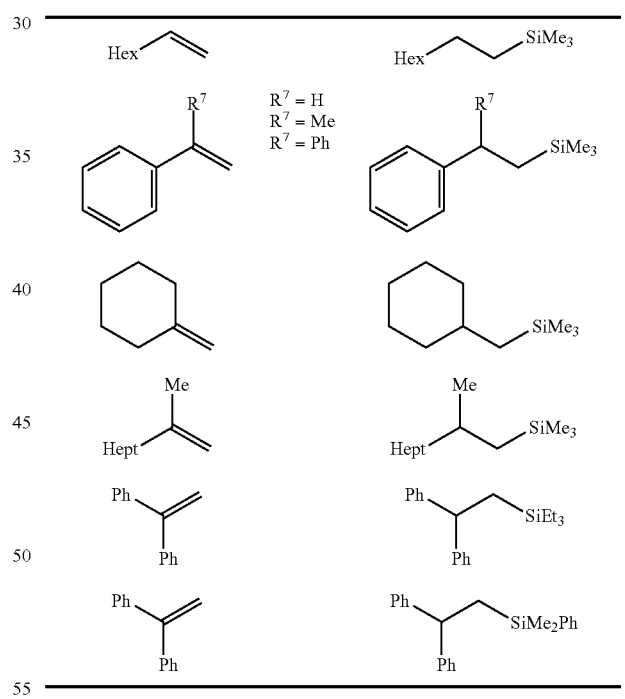

Particularly preferred alkenes for hydrosilylation with the new technique of the present invention are alkenes of general formula IIIa with $R^8$ representing —$CH_2$Hal and $R^6$ and $R^7$ representing hydrogen. Hydrosilylation of these alkenes, especially allylchloride, with a cyclohexa-2,5-dien-1-yl-trimethylsilane of formula I wherein $R^1$, $R^2$ and $R^3$ are equal to each other and represent methoxy or ethoxy results in commercially interesting trialkoxysilanes.

Further alkenes which can be hydrosilylated with the new technique of the invention are preferably alkenes of general formula IIIb

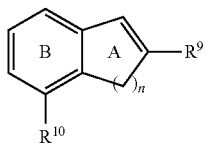

(IIIb)

wherein
a) in case that both rings A and B are present,
n is 1 or 2,
$R^9$ represents H, $C_1$-$C_{20}$-alkyl or $C_4$-$C_{20}$-cycloalkyl, preferably $C_1$-$C_4$-alkyl, represents H or halogen;
and
b) in case that ring B is not present,
in the cyclic alkene of ring A n is 1-4, preferably 2 or 3, and $R^9$ represents H or methyl.

Additionally, a further alkene which is preferably hydrosilylated according to the invention is norbornene (IIIc).

Some preferred alkenes of formulae IIIb and IIIc which are hydrosilylated with transfer hydrosilylating agents of formula I and their end products are given in Table 2:

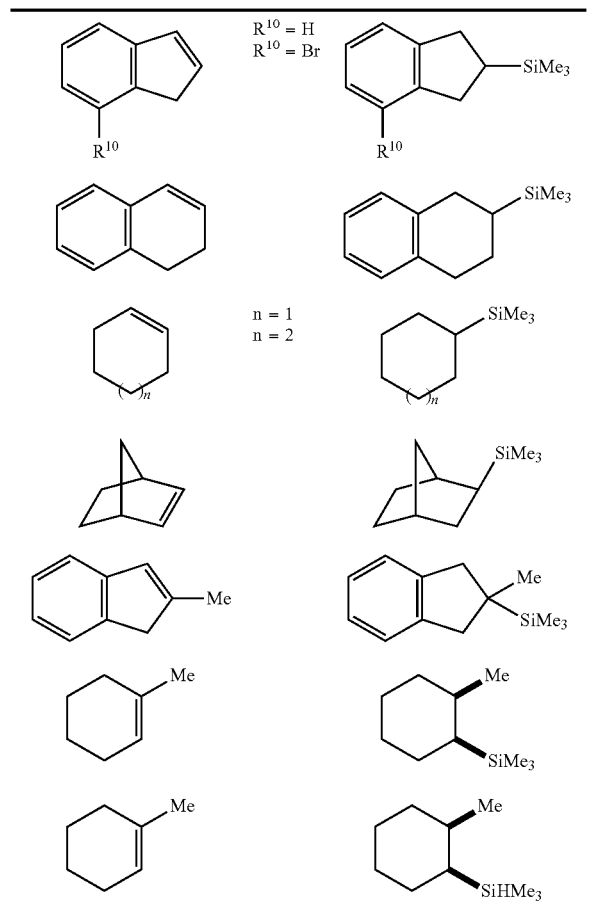

The cyclohexa-2,5-dien-1-yl-silanes of general formula I are not only useful as transfer hydrosilylating agents for alkenes but can also be used for Si—O bond formation in carbonyl reduction and dehydrogenative coupling with alcohols as well as hydrodehalogenation.

Hence, the hydrosilylation of carbonyl compounds is another object of the present invention, where cyclohexa-2,5-dien-1-yl-silanes of formula I in the presence of a strong Lewis acid as catalyst are used.

According to one embodiment of the present invention the carbonyl compounds which are hydrosilylated are compounds of general formula Va

wherein
R represents $C_1$-$C_{20}$ alkyl or aryl,
R' represents H, $C_1$-$C_{20}$ alkyl or aryl or
R and R' form together a $C_3$-$C_{20}$ cycloalkane ring.

According to the invention $C_1$-$C_{20}$ alkyl means branched or unbranched alkyl which may be substituted or unsubstituted. Aryl means substituted or unsubstituted aryl, preferably substituted or unsubstituted phenyl, tolyl xylyl, mesityl, naphtha-1-yl and naphtha-2-yl.

The following examples are offered to illustrate the present invention. They are not intended to be limiting in any respect.

PREPARATION EXAMPLES

1 General Information

All reactions were performed in flame-dried glassware using an MBraun glove box ($O_2$<0.5 ppm, $H_2O$<0.5 ppm) or conventional Schlenk techniques under a static pressure of argon (glove box) or nitrogen. Liquids and solutions were transferred with syringes. $CH_2Cl_2$, benzene, n-pentane, and THF were purified and dried using a MBraun solvent system. 1,2-Dichloroethane was distilled over $CaH_2$, degassed, and stored in glove box over 4 Å molecular sieves. Toluene was distilled over Na, degassed, and stored in glove box over 4 Å molecular sieves. $C_6D_6$ (purchased from Eurisotop) was dried over 4 Å molecular sieves. [D8] Toluene and $CD_2Cl_2$ (purchased from Eurisotop) were distilled from the appropriate drying reagent, degassed and stored in glove box over 4 Å molecular sieves. Technical grade solvents for extraction and chromatography (cyclohexane, n-pentane, ethyl acetate, and tert-butyl methyl ether) were distilled prior to use. All commercially available alkenes were distilled, degassed, and stored in glove box over 4 Å molecular sieves. Analytical thin-layer chromatography (TLC) was performed on silica gel SIL G-25 glass plates from Macherey-Nagel. Flash column chromatography was performed on silica gel 60 (40-63 μm, 230-400 mesh, ASTM) by Merck using the indicated solvents. $^1$H and $^{13}$C NMR spectra were recorded in $C_6D_6$ on Bruker AV 400 and Bruker AV 500 instruments. Chemical shifts are reported in parts per million (ppm) downfield from tetramethylsilane and are referenced to the residual solvent resonance as the internal standard ($C_8H_6$: δ=7.16 ppm for $^1$H NMR and $C_6D_6$: δ=128.06 ppm for $^{13}$C NMR). Data are reported as follows: chemical shift, multiplicity (br s=broad singlet, s=singlet, d=doublet, t=triplet, q=quartet, m=multiplet), coupling constant (Hz), and integration. Infrared (IR) spectra were recorded on an Agilent Technologies Cary 630 FT-IR spectrophotometer equipped with an ATR unit and are reported in wavenumbers (cm$^{-1}$). Gas liquid chromatography-mass spectrometry (GLC-MS) was performed on an Agilent Technologies GC-System 5975C with an Agilent Technologies Mass Selective Detector (EI) and a HP-5MS column. Gas liquid chromatography (GLC) was performed on a Shimadzu GC-17A gas chromatograph equipped with a SE-54 capillary column (30 m×0.32 mm, 0.25 μm film thickness) by CS-Chromatographie Service using the following programs: 35-min: $N_2$ carrier gas, column flow 1.7 mL/min, injection temperature 280° C., detector temperature 300° C.; temperature program: start temperature 40° C., heating rate 10° C./min, final temperature 280° C. for 10 min. High resolution mass spectrometry (HRMS) analysis was performed by the analytical facility at the Institut für Chemie, Technische Universität Berlin.

2 Experimental Details for the Synthesis of Cyclohexa-2,5-dien-1-ylsilanes 2.1 General Procedure for the Synthesis of Compounds (GP1)

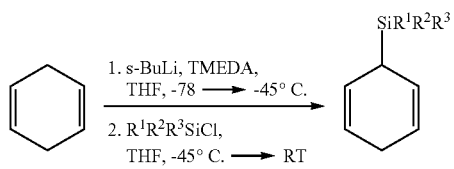

A flame-dried 100-mL Schlenk flask is charged with dry THF (0.7M) and cyclohexa-1,4-diene. The resulting solution is then cooled to −78° C. In a separate flame-dried 25-mL round-bottom flask equipped with a magnetic stir bar is introduced sec-BuLi (1.30M in hexanes, 1.0 equiv), followed by dropwise addition of TMEDA (1.0 equiv). The resulting dark-red slurry is subsequently added dropwise to the cooled THF solution of cyclohexa-1,4-diene, and the resulting mixture is then warmed to −45° C. and maintained at this temperature for 3 h; the solution turns yellow within that time. The corresponding chlorosilane (1.0 equiv) in THF (2.5M) is finally added dropwise at −45° C., and the resulting mixture is slowly warmed to room temperature. Saturated aqueous $NH_4Cl$ (20 mL) are added, and the aqueous layer is extracted with tert-butyl methyl ether (2×20 mL). The combined organic layers are washed with brine (20 mL) and water (20 mL). After removal of all volatiles, the crude material is purified by either flash column chromatography or distillation.

2.2 Characterization Data of Compounds Cyclohexa-25-dien-1-ylsilanes

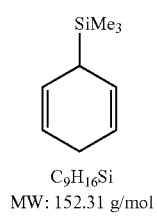

$C_9H_{16}Si$
MW: 152.31 g/mol

Cyclohexa-2,5-dien-1-yltrimethylsilane. Prepared according to GP1 from cyclohexa-1,4-diene (0.94 mL, 10.0 mmol, 1.0 equiv) and trimethylchlorosilane (1.27 mL, 10.0 mmol, 1.0 equiv). Purified by Kugelrohr distillation (30 mbar, 90° C.). Colorless oil, 1.15 g, 76% yield. IR (ATR): /$cm^{-1}$=3026, 2956, 2893, 2823, 1668, 1623, 1434, 1333, 1294, 1246, 1099, 1051, 980, 937, 893, 833, 784, 749, 714, 690. $^1$H NMR (500 MHz, $D_6D_6$) δ=5.68-5.65 (m, 2H), 5.55-5.52 (m, 2H), 2.78-2.55 (m, 2H), 2.18-2.11 (m, 1H), 0.01 (s, 9H). $^{13}$C NMR (126 MHz, $C_6D_6$) δ=126.5 (2C), 121.8 (2C), 31.8, 26.9, −3.5 (3C). GLC-MS (EI) for ($C_9H_{16}Si$): miz 152.1 [M]$^+$. HRMS (EI) exact mass for [M]$^+$: calcd m/z 152.10158, found 152.10186.

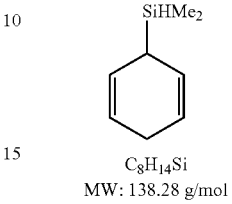

$C_8H_{14}Si$
MW: 138.28 g/mol

Cyclohexa-2,5-dien-1-yldimethylsilane. Prepared according to GP1 from an excess of cyclohexa-1,4-diene (2.60 mL, 27.5 mmol, 1.1 equiv) and dimethyichlorosilane (2.78 mL, 25.0 mmol, 1.0 equiv): Purified by flash column chromatography over silica gel using n-pentane as eluent. Colorless oil, 1.89 g, 55% yield. IR (ATR): /$cm^{-1}$=3026, 2960, 2890, 2855, 2823, 2112, 1624, 1432, 1294, 1248, 1102, 1053, 937, 874, 835, 793, 741, 688, 660. $^1$H NMR (500 MHz, $C_6D_6$) δ=5.68-5.61 (m, 2H), 5,56-5.49 (m, 2H), 4.09-3.99 (m, 1H), 2.67-2.56 (m, 2H), 2.31-2.21 (m, 1H), 0.03 (d, J=3.6, 6H). $^{13}$C NMR (126 MHz, $0_6 0_6$) 6 =126.0 (2C), 122.3 (2C), 29.6, 26.8, -6.4 (2C). GLC-MS (EI) for ($C_8H_{14}Si$): m/z 138.1 [M]$^+$. HRMS (EI) exact mass for [M]$^+$: calcd m/z 138.08593, found 138.08605.

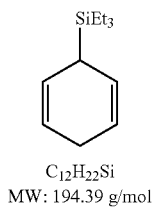

$C_{12}H_{22}Si$
MW: 194.39 g/mol

Cyclohexa-2,5-dien-1 -yltriethylsilane, Prepared according to GP1 from cyclohexa-1,4-diene (0.94 mL, 10.0 mmol, 1.0 equiv) and triethylchlorosilane (1.68 mL, 10.0 mmol, 1.0 equiv). Purified by Kugelrohr distillation (30 mbar, 150° C.). Colorless oil, 1.89 g, 97% yield. IR (ATR): /$cm^{-1}$=3026, 2952, 2910, 2876, 2821, 1624, 1458, 1416, 1378, 1334, 1294, 1239, 1100, 1053, 1008, 973, 938, 893, 777, 699, 664. $^1$H NMR (500 MHz, $C_6D_6$) δ=5.70-5.66 (m, 2H), 5.54-5.51 (m, 2H), 2.78-2.59 (m, 2H), 2.43-2.33 (m, 1 H), 0.96 (t, J=8.0, 9H), 0.58 (q, J=8.0, 6H). $^{13}$C NMR (126 MHz, $C_6D_6$) δ=126.8 (2C), 121.6 (2C), 28.7, 26.8, 7.8 (3C), 2.7 (3C). GLC-MS (EI) for ($C_{12}H_{22}Si$): m/z 194.1 [M]$^+$, 115.1 [M-$C_6H_7$]$^+$. HRMS (EI) exact mass for [M]$^+$: calcd m/z 194.14853, found 194.14836.

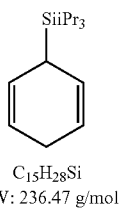

$C_{15}H_{28}Si$
MW: 236.47 g/mol

Cyclohexa-2,5-dien-1-yltrilsopropylsilane. Prepared according to GP1 from cyclohexa-1,4-diene (0.94 mL, 10.0 mmol, 1.0 equiv) and triisopropylchlorosilane (2.16 mL, 10.0 mmol, 1.0 equiv). Purified by flash column chromatography over silica gel using cyclohexane as eluent. White solid, 1.56 g, 66% yield. IR (ATR): /cm$^{-1}$=3021, 2942, 2887, 2864, 2823, 1459, 1431, 1382, 1335, 1293, 1254, 1110, 1072, 1015, 943, 885, 763, 669. $^1$H NMR (500 MHz, C$_6$D$_6$) δ=5.82-5.71 (m, 2H), 5.56-5.46 (m, 2H), 2.79-2.68 (m, 2H), 2.66-2.59 (m, 1H), 1.22-1.05 (m, 21H). $^{13}$C NMR (126 MHz, C$_6$D$_6$) δ=127.5 (2C), 121.6 (2C), 27.0, 26.6, 19.2 (6C), 11.7 (3C). GLC-MS (EI) for (C$_{15}$H$_{28}$Si): m/z 236.2 [M]$^+$. HRMS (EI) exact mass for [M]$^+$: calcd m/z 236, 19548, found 236,19557.

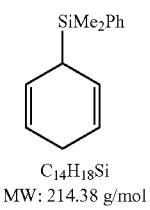

C$_{14}$H$_{18}$Si
MW: 214.38 g/mol

Cyclohexa-2,5-dien-1-yldimethyl(phenyl)silane. Prepared according to GP1 from cyclohexa-1,4-diene (1.13 mL, 12.0 mmol, 1.0 equiv) and dimethylphenylchlorosilane (1.99 mL, 12.0 mmol, 1.0 equiv). Purified by flash column chromatography over silica gel using cyclohexane as eluent. Colorless oil, 1.77 g, 69% yield. IR (ATR): /cm$^{-1}$=3025, 2958, 2890, 2851, 2820, 1427, 1294, 1246, 1111, 1051, 935, 892, 832, 809, 795, 759, 726, 696. $^1$H NMR (500 MHz, C$_6$D$_6$) δ=7.50-7.45 (m, 2H), 7.24-7.19 (m, 3H), 5.73-5.61 (m, 2H), 5.55-5.45 (m, 2H), 2.68-2.57 (m, 1H), 2.56-2.39 (m, 2H), 0.26 (s, 6H). $^{13}$C NMR (126 MHz, C$_6$D$_6$) δ=137.7, 134.3 (2C), 129.4 (2C), 128.3, 126.2 (2C), 122.3 (2C), 31.3, 26.8, −5.2 (2C). GLC-MS (EI) for (C$_{14}$H$_{18}$Si): m/z 214.2 [M]$^+$, 199.1 [M-CH$_3$]$^+$, 137.1 [M-C$_6$H$_5$]$^+$, HRMS (EI) exact mass for [M]$^+$: calcd m/z 214.11723, found 214.11621.

3 Experimental Details for the Synthesis of Silanes by Transfer Hydrosilylation 3.1 General Procedure for the Catalytic Transfer Hydrosilylation of Alkenes with Cyclohexa-2,5-dien-1-ylsilanes (GP2)

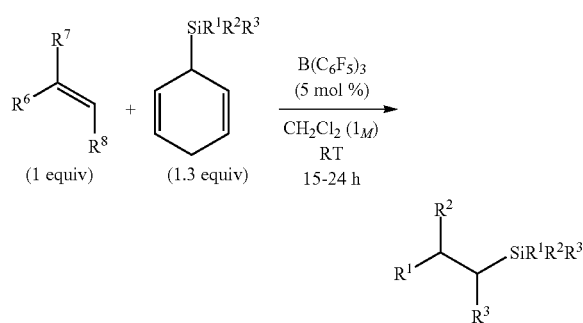

In glove box, a 1.3-mL GLC vial is charged with B(C$_6$F$_5$)$_3$ (5.0 mol %) and a magnetic stir bar. Into a separate vial are weighed the alkene (1.0 equiv) and the cyclohexa-2,5-dien-1-ylsilane (1.3 equiv). Both reagents are dissolved in CH$_2$Cl$_2$ (1.0 M) and the resulting solution is added to the catalyst. The vial is then capped, and the solution is stirred in the glove box. The reaction is monitored by GLC and typically requires 15 to 24 h stirring at room temperature.

The mixture is finally diluted with n-pentane (0.3 mL), filtered over a small Celite®/SiO$_2$ column (1 cm Celite® covered with 0.5 cm SiO$_2$, eluting with n-pentane), and all volatiles are removed under reduced pressure. If necessary, the crude target compound is purified by either flash column chromatography or Kugelrohr distillation.

3.2 Characterization Data of Compounds

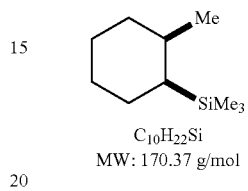

C$_{10}$H$_{22}$Si
MW: 170.37 g/mol cis-Trimethyl(2-methylcyclohexyl)silane. Prepared according to GP2 from 1-methyl-cyclohexene (48.1 mg, 0.50 mmol, 1.0 equiv) and cyclohexa-2,5-dien-1-yltrimethylsilane (99.0 mg, 0.65 mmol, 1.3 equiv). Reaction was stopped after 24 h. Purified by flash column chromatography using n-pentane as eluent. cis configuration was assigned by analogy with the B(C$_6$F$_5$)$_3$-catalyzed hydrosilylation of 1-methylcyclohexene with dimethylphenylsilane and consistent NMR data. Colorless oil, 74 mg, 87% yield. IR (ATR): /cm$^{-1}$=2955, 2919, 2850, 2812, 1444, 1405, 1378, 1247, 1200, 1156, 1106, 1059, 1018, 954, 871, 828, 744, 687. $^1$H NMR (500 MHz, C$_6$D$_6$) δ=1.99-1.93 (m, 1H), 1.68 (ddd, J=11.4, 5.7, 2.4, 1H), 1.60-1.32 (m, 6H), 1.27-1.15 (m, 1H), 0.93 (d, J=7.2, 3H), 0.86-0.69 (m, 1H), 0.01 (s, 9H). $^{13}$C NMR (126 MHz, C$_6$D$_6$) δ=35.4, 30.8, 30.0, 28.6, 22.5, 21.7, 16.5, −1.9 (3C). GLC-MS (EI) for (C$_{10}$H$_{22}$Si): m/z 170.1 [M]$^+$, 155.1 [MCH$_3$]$^+$. HRMS (EI) exact mass for [M]$^+$: calcd m/z 170.14853, found 170.14856.

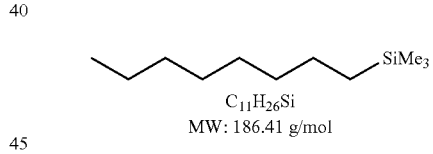

C$_{11}$H$_{26}$Si
MW: 186.41 g/mol

Trimethyl(octyl)silane. Prepared according to GP2 from oct-1-ene (22.4 mg, 0.20 mmol, 1.0 equiv) and cyclohexa-2,5-dien-1-yltrimethylsilane (39.6 mg, 0.26 mmol, 1.3 equiv). Conversion was complete after 15 h. Crude material did not require purification. Colorless oil, 31 mg, 84% yield. IR (ATR): /cm$^{-1}$=2956, 2922, 2855, 1459, 1412, 1295, 1248, 1175, 1110, 1001, 833, 755, 723, 690. $^1$H NMR (500 MHz, C$_6$D$_6$) δ=1.44-1.18 (m, 12H), 1.02-0.86 (m, 3H), 0.59-0.47 (m, 2H), 0.03 (s, 9H). $^{13}$C NMR (126 MHz, C$_6$D$_6$) δ=34.1, 32.4, 29.8, 29.8, 24.4, 23.1, 17.0, 14.4, −1.5 (3C). GLC-MS (EI) for (C$_{22}$H$_{24}$Si): m/z 171.1 [M-CH$_3$]$^+$. HRMS (EI) exact mass for [M]$^{30}$ : calcd m/z 186.17983, found 186.18008.

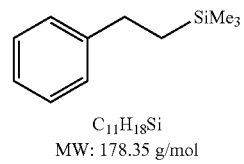

C$_{11}$H$_{18}$Si
MW: 178.35 g/mol

Trimethyl(phenethyl)silane. Prepared according to GP2 from styrene (20.8 mg, 0.20 mmol, 1.0 equiv) and cyclohexa-2,5-dien-1-yltrimethylsilane (39.6 mg, 0.26 mmol, 1.3 equiv). Conversion was complete after 17 h. Crude material did not require purification. Colorless oil, 28 mg, 78% yield. IR (ATR): /cm=3028, 2954, 2900, 1603, 1496, 1454, 1412, 1302, 1248, 1174, 1124, 1030, 998, 902, 857, 830, 747, 693. $^1$H NMR (400 MHz, C$_6$D$_6$) δ=7.24-7.17 (m, 2H), 7.14-7.07 (m, 3H), 2.61-2.50 (m, 2H), 0.85-0.70 (m, 2H), −0.03 (s, 9H). $^{13}$C NMR (101 MHz, C$_5$D$_6$) δ=145.3, 128.6 (2C), 128.2 (2C), 125.9, 30.5, 18.8, −1.7 (3C). GLC-MS (EI) for (C$_{11}$H$_{18}$Si): m/z 178.1 [M]$^+$, 163.1 [M-CH$_3$]$^+$. HRMS (ED exact mass for [M]$^+$: calcd m/z 178.11723, found 178.11747.

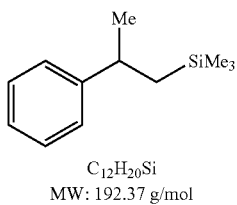 [SMILES: CC(C[Si](C)(C)C)c1ccccc1]

C$_{12}$H$_{20}$Si
MW: 192.37 g/mol

Trimethyl(2-phenylpropyl)silane. Prepared according to GP2 from α-methylstyrene (23.6 mg, 0.20 mmol, 1.0 equiv) and cyclohexa-2,5-dien-1-yltrimethylsilane (39.6 mg, 0.26 mmol, 1.3 equiv). Conversion was complete after 17 h. Crude material did not require purification. Colorless oil, 28 mg, 85% yield. IR (ATR): /cm$^{-1}$=3028, 2955, 2898, 1603, 1493, 1451, 1411, 1372, 1300, 1247, 1186, 1147, 1083, 1028, 913, 834, 761, 697. $^1$H NMR (400 MHz, C$_6$D$_6$) δ=7.22-7.13 (m, 2H), 7.12-7.03 (m, 3H), 2.78 (dp, J=8.6, 6.8, 1H), 1.23 (d, J =6.9, 3H), 0.92 (dd, J=14.6, 8.6, 1H), 0.78 (dd, J=14.7, 6.6, 1H), −0.11 (s, 9H). $^{13}$C NMR (101 MHz, C$_6$D$_6$) δ=149.7, 128.7 (2C), 127.1 (2C), 126.2, 36.9, 27.1, 27.0, −0.9 (3C). GLC-MS (EI) for (C$_{12}$H$_{20}$Si): m/z 192.1 [M]$^+$, 177.1 [M-CH$_3$]$^+$, 105.1 [M-C$_4$H$_{11}$Si]$^+$. HRMS (EI) exact mass for [M]$^+$: calcd m/z 192.13288, found 192.13333.

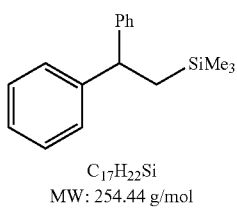 [SMILES: C[Si](C)(C)CC(c1ccccc1)c1ccccc1]

C$_{17}$H$_{22}$Si
MW: 254.44 g/mol (2,2-Diphenylethyl)trimethylsilane. Prepared according to GP2 from 1,1-diphenylethylene (36.1 mg, 0.20 mmol, 1.0 equiv) and cyclohexa-2,5-dien-1-yltrimethylsilane (39.6 mg, 0.26 mmol, 1.3 equiv). Conversion was complete after 22 h. Crude material did not require purification. Colorless oil, 48 mg, 94% yield. IR (ATR): /cm$^{-1}$=3062, 3027, 2952, 2896, 1598, 1492, 1450, 1413, 1247, 1173, 1131, 1072, 1031, 1015, 849, 828, 780, 748, 694. $^1$H NMR (500 MHz, C$_6$D$_6$) δ=7.19 (d, J=7.2, 4H), 7.12 (t, J=7.8, 4H), 7.01 (t, J=7.3, 2H), 4.02 (t, J=8.1, 1H), 1.30 (d, J=8.1, 2H), −0.16 (s, 9H). $^{13}$C NMR (126 MHz, C$_6$D$_6$) δ 147.5 (2C), 128.6 (4C), 128.0 (2C), 126.3 (4C), 47.8, 24.3, −1.1 (3C). GLC-MS (EI) for (C$_{17}$H$_{22}$Si): m/z 254.2 [M]$^+$, 239.1 [M-CH$_3$]$^+$. HRMS (EI) exact mass for [M]$^+$: calcd m/z 254.14853, found 254.14933.

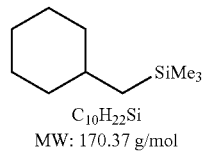

C$_{10}$H$_{22}$Si
MW: 170.37 g/mol (Cyclohexylmethyl)trimethylsilane. Prepared according to GP2 from methylenecyclohexane (19.2 mg, 0.20 mmol, 1.0 equiv) and cyclohexa-2,5-dien-1-yltrimethylsilane (39.6 mg, 0.26 mmol, 1.3 equiv). Reaction was stopped after 24 h. Crude material did not require purification. Colorless oil, 29 mg, 85% yield. IR (ATR); /cm$^{-1}$=2921, 2853, 1448, 1413, 1247, 1152, 1033, 969, 889, 858, 832, 772, 755, 689. $^1$H NMR (400 MHz, C$_6$D$_6$) δ=1.80-1.54 (m, 5H), 1.45-1.33 (m, 1H), 1.33-1.05 (m, 3H), 1.03-0.82 (m, 2H), 0.49 (d, J=6.9, 2H), 0.04 (s, 9H). $^{13}$C NMR (126 MHz, C$_6$D$_6$) δ=37.2 (2C), 34.8, 27.0 (2C), 26.7, 26.0, −0.4 (3C). GLC-MS (EI) for (C$_{10}$H$_{22}$Si): m/z 170.2 [M]$^+$, 155.1 [M-CH$_3$]$^+$. HRMS (EI) exact mass for [M]$^+$: calcd m/z 170.14853, found 170.14842.

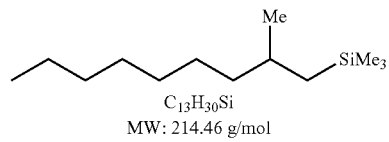

C$_{13}$H$_{30}$Si
MW: 214.46 g/mol

Trimethyl(2-thethylnonyl)silane. Prepared according to GP2 from 2-methylnon-1-ene (281 mg, 0.20 mmol, 1.0 equiv) and cyclohexa-2,5-dien-1-yltrimethylsilane (39.6 mg, 0.26 mmol, 1.3 equiv), Conversion was complete after 17 h. Crude material did not require purification. Colorless oil, 35 mg, 81% yield. IR (ATR): /cm$^{-1}$=2955, 2925, 2855, 1459, 1414, 1376, 1295, 1248, 1216, 1108, 1030, 833, 784, 759, 689, $^1$H NMR (500 MHz, C$_6$D) δ=1.69-1.55 (m, 1H), 1.38-1.15(m, 12H), 0.97 (d, J=6.6, 3H), 0.94-0.89 (m, 3H), 0.67 (dd, J=14.6, 5.1, 1H), 0.42 (dd, J=14.7, 8.5, 1H), 0.06 (s, 9H). $^{13}$C NMR (126 MHz, C$_6$D$_6$) δ=41.1, 32.4, 30.4, 30.0, 29.9, 27.7, 25.5, 23.3, 23.2, 14.4, −0.4 (3C). GLC-MS (EI) for (C$_{13}$H$_{30}$Si): m/z 199.2 [M-CH$_3$]$^+$, 115.1 [M-C$_7$H$_{15}$]$^+$. HRMS (EI) exact mass for [M]$^+$; calcd m/z 214.21113, found 214.21203.

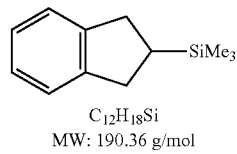 [SMILES: C[Si](C)(C)C1Cc2ccccc2C1]

C$_{12}$H$_{18}$Si
MW: 190.36 g/mol (2,3-Dihydro-1H-inden-2-yl)trimethylsilane. Prepared according to GP2 from indene (23.2 mg, 0.20 mmol, 1.0 equiv) and cyclohexa-2,5-dien-1-yltrimethylsilane (39.6 mg, 0.26 mmol, 1.3 equiv). Conversion was complete after 15 h. Purified by flash column chromatography using n-pentane as eluent. Colorless oil, 25 mg, 69% yield. IR (ATR): /cm$^{-1}$=3023, 2953, 2895, 2839, 1482, 1459, 1444, 1404, 1318, 1247, 1144, 1025, 990, 931, 908, 830, 747, 689. $^1$H NMR (400 MHz, C$_6$D$_6$) δ=7.22-7.08 (m, 4H), 2.81 (dd, J=15.2, 9.0, 2H), 2.64 (dd, J=15.2, 10.3, 2H), 1.37 (p, J=10.3, 1H), −0.05 (s, 9H). $^{13}$C NMR (101 MHz, C$_6$D$_6$)

δ=145.0 (2C), 126.4 (2C), 124.5 (2C), 34.9 (2C), 26.3, −3.0 (3C). GLC-MS (EI) for (C$_{12}$H$_{18}$Si): m/z 190.1 [M]$^+$, 175.1 [M-CH$_3$]$^+$. HRMS (EI) exact mass for [M]$^+$: calcd m/z 190.11723, found 190.11719.

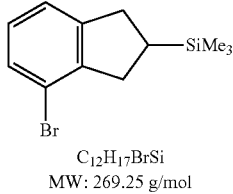 [SMILES: C[Si](C)(C)C1Cc2cccc(Br)c2C1]

C$_{12}$H$_{17}$BrSi
MW: 269.25 g/mol (4-Bromo-2,3-dihydro-1H-inden-2-yl)trimethylsilane. Prepared according to GP2 from 7-bromo-1H-indene (39.0 mg, 0.20 mmol, 1.0 equiv) and cyclohexa-2,5-dien-1-yltrimethylsilane (39.6 mg, 0.26 mmol, 1.3 equiv). Conversion was complete after 17 h. Purified by Kugelrohr distillation (10 mbar, 150° C.). Colorless oil, 35 mg, 65% yield. IR (ATR): /cm$^{-1}$=2952, 2894, 2837, 1567, 1447, 1319, 1248, 1162, 1137, 1117, 1057, 987, 914, 831, 763, 689. $^1$H NMR (500 MHz, C$_6$D$_6$) δ =7.25 (d, J=7.9, 1H), 6.88 (d, J=7.3, 1H), 6/4 (t, J=7.6, 1H), 3.03 (dd, J=16.3, 9.1, 1H), 2.73 (dt, J=16.1, 9.9, 2H), 2.59 (dd, J=15.9, 10.7, 1H), 1.26 (p, J=9.8, 1H), −0.11 (s, 9H). $^{13}$C NMR (126 MHz, C$_6$D$_6$) δ=147.1, 145.5, 129.6, 128.3, 123.2, 120.3, 36.6, 36.1, 25.2, −3.1 (3C). GLC-MS (EI) for (C$_{12}$H$_{17}$BrSi): m/z 270.0 [M]$^+$, 255.0 [M-CH$_3$]$^+$. HRMS (EI) exact mass for [M]: calcd m/z 268.02774, found 268.02740.

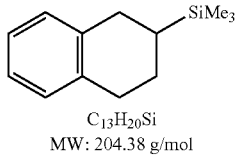 [SMILES: C[Si](C)(C)C1CCc2ccccc2C1]

C$_{13}$H$_{20}$Si
MW: 204.38 g/mol

Trimethyl(1,2,3,4-tetrahydronaphthalen-2-yl)silane. Prepared according to GP2 from 1,2-dihydronaphthalene (26.0 mg, 0.20 mmol, 1.0 equiv) and cyclohexa-2,5-dien-1-yltrimethyl-silane (39.6 mg, 0.26 mmol, 1.3 equiv). Reaction was stopped after 24 h. Purified by flash column chromatography using n-pentane as eluent. Colorless oil, 27 mg, 66% yield. IR (ATR): /cm$^{-1}$=3018, 2953, 2912, 2834, 1581, 1494, 1450, 1433, 1350, 1291, 1247, 1158, 1109, 1078, 1041, 945, 922, 889, 829, 740, 687. $^1$H NMR (400 MHz, C$_6$D$_6$) δ=7.12-7.06 (m, 2H), 7.06-7.00 (m, 2H), 2.71-2.41 (m, 4H), 1.81-1.66 (m, 1H), 1.28 (tdd, J=12.9, 10.8, 6.3, 1H), 0.75 (tdd, J=12.5, 5.0, 2.6, 1H), −0.05 (s, 9H). $^{13}$C NMR (101 MHz, C$_6$D$_6$) δ=137.8, 137.3, 129.6, 129.2, 125.8, 125.8, 30.6 (2C), 24.4, 22.3, −3.6 (3C). GLC-MS (EI) for (C$_{13}$H$_{20}$Si): m/z 204.1 [M]$^+$, 189.1 [M-CH$_3$]$^+$. HRMS (EI) exact mass for [M]$^+$: calcd m/z 204.13288, found 204.13337.

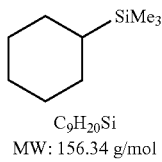

C$_9$H$_{20}$Si
MW: 156.34 g/mol

Cyclohexyltrimethylsilane. Prepared according to GP2 from cyclohexene (16.4 mg, 0.20 mmol, 1.0 equiv) and cyclohexa-2,5-dien-1-yltrimethylsilane (39.6 mg, 0.26 mmol, 1.3 equiv). Reaction was stopped after 19 h. Crude material did not require purification. Colorless oil, 19 mg, 61% yield. IR (ATR): /cm$^{-1}$=2954, 2919, 2846, 1446, 1293, 1247, 1100, 1039, 997, 889, 858, 826, 745, 687, $^1$H NMR (500 MHz, C$_6$D$_6$) δ=1.83-1.49 (m, 5H), 1.31-0.93 (m, 5H), 0.49 (tt, J=12.8, 3.1, 1H), −0.04 (s, 9H). $^{13}$C NMR (126 MHz, C$_6$D$_6$) δ=28.5 (2C), 27.7 (2C), 27.4, 26.4, −3.5 (3C). GLC-MS (EI) for (C$_8$H$_{20}$Si): m/z 156.1 [M]$^+$, 141.1 [M-CH$_3$]$^+$. HRMS (EI) exact mass for [M]$^+$: calcd m/z 156.13288, found 156.13357.

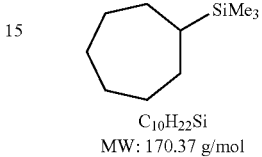

C$_{10}$H$_{22}$Si
MW: 170.37 g/mol

Cycloheptyltrimethylsilane. Prepared according to GP2 from cycloheptene (48.1 mg, 0.50 mmol, 1.0 equiv) and cyclohexa-2,5-dien-1-yltrimethylsilane (99.0 mg, 0.65 mmol, 1.3 equiv). Reaction was stopped after 18 h. Purified by Kugelrohr distillation (1 atm N$_2$, 125° C.). Colorless oil, 61 mg, 71% yield. IR (ATR): 2916, 2850, 1449, 1363, 1289, 1247, 1096, 1041, 1016, 897, 829, 741, 686. $^1$H NMR (500 MHz, C$_6$D$_6$) δ=1.80-1.67 (m, 4H), 1.65-1.56 (m, 2H), 1.54-1.36 (m, 4H), 1.26-1.13 (m, 2H), 0.56 (tt, J=11.0, 3.3, 1H), −0.01 (s, 9H). $^{13}$C NMR (126 MHz, C$_6$D$_6$) δ=30.4 (2C), 29.2 (2C), 28.8 (2C), 27.0, −3.2 (3C). GLC-MS (EI) for (C$_{10}$H$_{22}$Si): m/z 170.2 [M]$^+$, 155.1 [M-CH$_3$]$^+$. HRMS (EI) exact mass for [M]$^+$: calcd m/z 170.14853, found 170.14848.

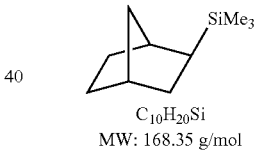

C$_{10}$H$_{20}$Si
MW: 168.35 g/mol exo-Bicyclo[2.2.1]heptan-2-yitrimethylsilane. Prepared according to GP2 from norbornene (47,1 mg, 0.50 mmol, 1.0 equiv) and cyclohexa-2,5-dien-1-yltrimethylsilane (1, 99.0 mg, 0.65 mmol, 1.3 equiv). Conversion was complete after 22 h. Purified by flash column chromatography using n-pentane as eluent. Exo configuration was assigned according to literature data. Colorless oil, 58 mg, 69% yield. IR (ATR): /cm$^{-1}$=2949, 2867, 1453, 1402, 1292, 1246, 1112, 1028, 998, 970, 908, 826, 743, 686. $^1$H NMR (500 MHz, C$_8$D$_6$) δ=2.21 (br s, 1H), 2.13 (br s, 1H), 1.52 (dq, J=6.1, 1.8, 2H), 1.39-1.29 (m, 2H), 1.24-1.14 (m, 3H), 1.08 (dt, J=9.3, 1.8, 1H), 0.44 (ddd, J=9.4, 7.6, 1.6, 1H), −0.02 (s, 9H). $^{13}$C NMR (126 MHz, C$_6$D$_6$) δ=38.2, 38.2, 37.3, 34.6, 32.8, 29.6, 29.3, −2.5 (3C). GLC-MS (EI) for (C$_{10}$H$_{20}$Si): m/z 168.1 [M]$^+$, 153.1 [M-CH$_3$]$^+$. HRMS (EI) exact mass for [M]$^+$: calcd m/z 168.13288, found 168.13246.

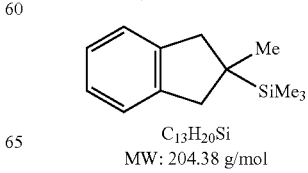

C$_{13}$H$_{20}$Si
MW: 204.38 g/mol

Trimethyl(2-methyl-2,3-thhydro-1H-inden-2-yl)silane. Prepared according to GP2 from 2-methyl-1H-indene (26.0 mg, 0.20 mmol, 1.0 equiv) and cyclohexa-2,5-dien-1-yltrimethyl-silane (39.6 mg, 0.26 mmol, 1.3 equiv). Conversion was complete after 22 h. Purified by flash column chromatography using n-pentane as eluent and obtained in mixture with minor amounts of the other regiosiomer trimethyl(2-methyl-2,3-dihydro-1H-inden-1-yl)silane. Colorless oil, 32 mg, 73% yield, 5% yield of the regioisomer. IR (ATR): /cm$^{-1}$=3021, 2953, 2896, 2838, 1586, 1482, 1456, 1402, 1371, 1318, 1248, 1081, 1024, 936, 873, 830, 790, 739, 686. $^1$H NMR (500 MHz, C$_6$D$_6$) δ=7.15-7.10 (m, 4H), 2.90 (d, J=15.5, 2H), 2.40 (d, J=15.4, 2H), 0.96 (s, 3H), −0.07 (s, 9H). $^{13}$C NMR (126 MHz, C$_6$D$_6$) δ=143.5 (2C), 126.6 (2C), 125.1 (2C), 43.0 (2C), 28.1, 23.5, −3.9 (3c). GLC-MS (EI) for (C$_{13}$H$_{20}$Si): m/z 204.1 [M]$^+$, 189.1 [M-CH$_3$]$^+$. HRMS (EI) exact mass for [M]$^+$: calcd m/z 204 13288, found 204.13320.

Trimethyl(2-methyl-2,3-dihydro-1H-inden-1-yl)silane. Obtained as the minor component of a mixture, only partial data could have been collected. $^1$H NMR (500 MHz, C$_6$D$_6$) δ=2.75 (dd, J=14.4, 7.4, 1H), 2.68 (dq, J=9.2, 7.2, 1H), 2.48 (ddd, J=14.6, 9.2, 1.3, 1H), 2.32 (d, J=7.7, 1H), 1.08 (d, J=6.9, 3H), 0.04 (s, 9H), aromatic signals under those of the major isomer.

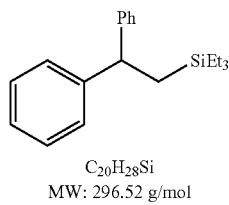

C$_{20}$H$_{28}$Si
MW: 296.52 g/mol (2,2-Diphenylethyl)triethylsilane. Prepared according to GP2 from 1,1-diphenylethylene (36.1 mg, 0.20 mmol, 1.0 equiv) and cyclohexa-2,5-dien-1-yltriethylsilaine (50.5 mg, 0.26 mol, 1.3 equiv). After 42 h, GC monitoring showed no further conversion of the starting material and after work-up the desired product was obtained in mixture with 1,1-diphenylethylene. It could be removed by Kugelrohr distillation (25 mbar, 175° C.). Colorless oil, 38 mg, 64% yield. IR (ATR): /cm$^{-1}$=3026, 2951, 2908, 2874, 1598, 1492, 1451, 1415, 1377, 1341, 1237, 1172, 1132, 1072, 1007, 964, 912, 854, 827, 776, 737, 695. $^1$H NMR (400 MHz, C$_6$D$_6$) δ=7.28-7.20 (m, 4H), 7.14-7.09 (m, 4H), 7.07-6.98 (m, 2H), 4.07 (t, J=1H), 1.38 (d, J=7.9, 2H), 0.87 (t, J=7.9, 8H), 0.37 (q, J=3.0, 6H). $^{13}$C NMR (101 MHz, C$_6$D$_8$) δ=147.7 (2C), 128.7 (4C), 127.9 (4C), 126.3 (2C), 47.6, 19.4, 7.7 (3C), 3.9 (3C). GLC-MS (EI) for (C$_{20}$H$_{28}$Si): m/z 267.1 [M-C$_2$H$_5$]$^+$.

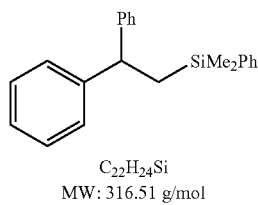

C$_{22}$H$_{24}$Si
MW: 316.51 g/mol (2,2-Diphenylethyl)dimethyl(phenyl)silane. Prepared according to GP2 from 1,1-diphenylethylene (36.1 mg, 0.20 mmol, 1.0 equiv) and cyclohexa-2,5-dien-1-yldimethyl-(phenyl)silane (55.7 mg, 0.26 mmol, 1,3 equiv), complete conversion after 24 h. Purified by flash column chromatography using n-pentaneitert-butyl methyl ether 99:1 as eluent. Colorless oil, 59 mg, 94% yield. IR (ATR): /cm$^{-1}$=3064, 3025, 2954, 2900, 1598, 1492, 1450, 1427, 1248, 1172, 1111, 1071, 1030, 913, 863, 834, 809, 781, 728, 694. $^1$H NMR (400 MHz, C$_5$D$_6$) δ=7.42-7.36 (m, 2H), 7.25-7.20 (m, 3H), 7.14-7.05 (m, 8H), 7.03-6.97 (m, 2H), 4.02 (t, J=8.0, 1H), 1.55 (d, J=8.0, 2H), 0.01 (s, 6H). $^{13}$C NMR (101 MHz, C$_6$D$_6$) δ=147.3 (2C), 139.4, 134.0 (2C), 129.2, 128.6 (4C), 128.2 (2C), 128.0 (4C), 126.3 (2C), 47.6, 23.7, −2.5 (2C). GLC-MS (EI) for (C$_{22}$H$_{24}$Si): m/z 301.1 [M-CH$_3$]$^+$.

3.3 Procedure for the Two-Fold Silylation of Styrene with Cyclohexa-2,5-dien-1-yldimethyisilane

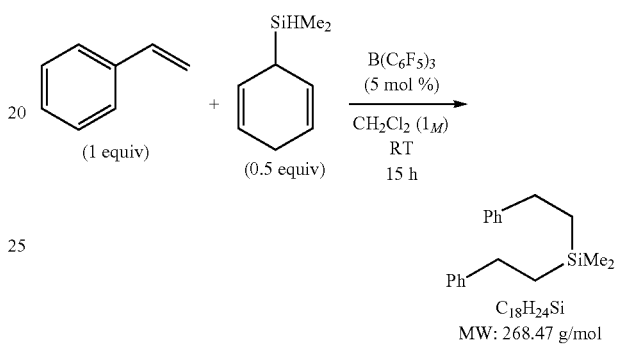

C$_{18}$H$_{24}$Si
MW: 268.47 g/mol

Dimethyldiphenethylsilane. In glove box, a 1.3-mL GLC vial was charged with B(C$_6$F$_5$)$_3$ (5.1 mg, 5.0 μmol, 5.0 mol %) and a magnetic stir bar. Into a separate vial were weighed styrene (20.6 mg, 0.20 mmol, 1.0 equiv) and cyclohexa-2,5-dien-1-yldimethylsilane (13.8 mg, 0.10 mmol, 0.50 equiv). Both reagents were dissolved in CH$_2$Cl$_2$ (0.2 mL), and the resulting solution was added to the catalyst. The vial was then capped and the solution stirred in the glove box. After 15 h, two drops of Et$_3$N were added to the reaction mixture, and the vial was stirred for 5 min. The mixture was finally diluted with n-pentane (0.3 mL), filtered over a small Celite®/SiO$_2$ column (1 cm Celite® covered with 0.5 cm SiO$_2$, eluting with n-pentane), and after removal of all volatiles the crude title compound was purified by flash column chromatography using n-pen-taneitart-butyl methyl ether 98:2 as eluent. Colorless oil, 21 mg, 78% yield. IR (ATR): /cm$^{-1}$=3063, 3026, 2952, 2919, 1603, 1495, 1453, 1412, 1312, 1249, 1173, 1124, 1066, 1030, 997, 898, 831, 796, 768, 747, 722, 695. $^1$H NMR (400 MHz, C$_8$D$_6$) δ=7.24-7.18 (m, 4H), 7.14-7.07 (m, 6H), 2.58-2.48 (m, 4H), 0.85-0.70 (m, 4H), −0.06 (s, 6H). $^{13}$C NMR (101 MHz, CD$_8$) δ=145.3 (2C), 128.7 (4C), 128.2 (4C), 126.0 (2C), 30.4 (2C), 17.4 (2C), −3.4 (2C). GLC-MS (EI) for (C$_{18}$H$_{24}$Si): m/z 253.2 [MCH$_3$]$^+$, 163.1 [M-C$_8$H$_9$]$^+$.

3.4 Procedure for the Transfer Hydrosilylation of 1-Methylcyclohexene with Cyclohexa-2,5-idien-1-yldimethylsilane

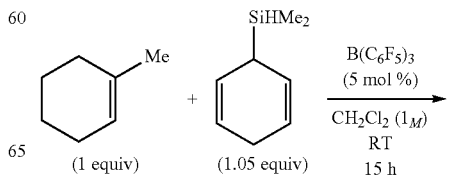

-continued

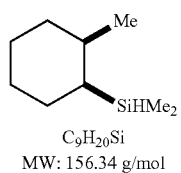

C₉H₂₀Si
MW: 156.34 g/mol

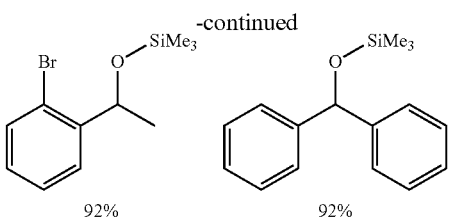

92%   92% cis-Dimethyl(2-methyloyclohexyl)silane. In glove box, a 1.3-mL GLC vial was charged with B(C₆F₅)₃ (12.8 mg, 25.0 μmol, 5.0 mol %) and a magnetic stir bar. Into a separate vial were weighed 1-methylcyclohexene (48.1 mg, 0.50 mmol, 1.0 equiv) and cyclohexa-2,5-dien-1-yldimethylsilane (72.6 mg, 0.525 mmol, 1.05 equiv). Both reagents were dissolved in CH₂Cl₂ (0.2 mL), and the resulting solution was added to the catalyst. The vial was then capped, and the solution stirred in the glove box. After 15 h, four drops of Et₃N were added to the reaction mixture, and the vial was stirred for 5 min. The mixture was finally diluted with n-pentane (0.3 mL), filtered over a small Celite®/SiO₂ column (1 cm Celite covered with 0.5 cm SiO₂, eluting with n-pentane), and after removal of all volatiles the crude title compound was purified by Kugelrohr distillation under a N₂ atmosphere (120° C.), cis configuration was assigned by analogy with the B(C₆F₅)₃-catalyzed hydrosilylation of 1-methylcyclohexene with diphenylsilane and consistent NMR data. Colorless oil, 38 mg, 49% yield. IR (ATR): /cm⁻¹=2958, 2921, 2851, 2108, 1444, 1390, 1249, 1166, 1103, 1080, 955, 877, 833, 784, 759, 699. ¹H NMR (500 MHz, C₆D₆) δ=4.07 (h, J=3.7, 1H), 1.94-1.87 (m, 1H), 1.64-1.34 (m, 7H), 1.29-1.21 (m, 1H), 0.98 (d, J=7.3, 3H), 0.85 (dq, J=10.2, 3.9, 1H), 0.05 (t, J=3.8, 6H). ¹³C NMR (126 MHz, C₆D₆) δ=34.6, 31.2, 29.6, 27,7, 24,3, 22.7, 17.3, −4.4, −4.9 . GLC-MS (EI) for (C₉H₂₀Si): m/z 156.1 [M]⁺, 141.1 [M-CH₃]⁺. HRMS (EI) exact mass for [M]⁺: calcd m/z 156.13288, found 156.13363.

3.5 General Procedure for the Catalytic Transfer Hydrosilylation of Carbonyl Compounds with Cyclohexa-2,5-dien-1-yltrimethylsilane Hydrosilylation of Ketones

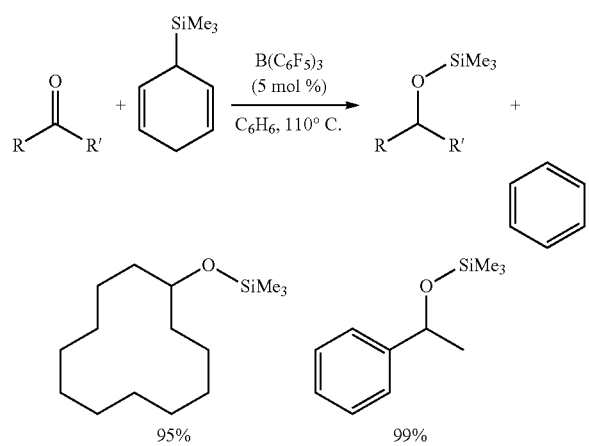

95%   99%

In glove box, a 1-mL Ace© pressure tube is loaded with the ketone (0.30 mmol) and cyclohexa-2,5-dien-1-yltrimethylsilane (54.80 mg, 0.36 mmol, 1.20 equiv). In a separate 1.3-mL GC vial is weighed tris(pentafluorophenyl)borane (7.70 mg, 15.00 μmol, 5.00 mol %), and the latter is dissolved in 0.45 mL of C₆H₆. The resulting solution is then transferred to the pressure tube via syringe, the tube is sealed and heaten to 110° C. out of the glove box. The reaction is monitored by GC, and when full conversion is noticed, the sealed tube is cooled down to room temperature and carefully opened. The reaction mixture is filtered over a short column of neutral alumina (MP Ecochrom, activity grade I, MP Biomedicals Germany GmbH) and the volatiles are removed under reduced pressure, to yield the trimethylsilyether in an analytically pure form.

3.6 Characterization Data of Compounds

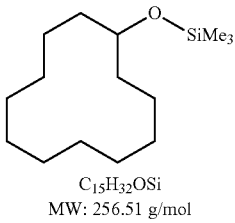 [SMILES: C[Si](C)(C)OC1CCCCCCCCCCC1]

C₁₅H₃₂OSi
MW: 256.51 g/mol (Cyclododecyloxy)trimethylsilane. Prepared from cyclododecanone (54.70 mg, 0.30 mmol) and obtained as a colorless oil (73 mg, 95% yield) after 15 h at 110° C. in C₆H₆. IR (ATR). ṽ/cm⁻¹=2929, 2860, 1468, 1375, 1248, 1057, 834, 746. ¹H NMR (500 MHz, C₆D₆) δ=3.75-3.67 (m, 1H), 1.57-1.45 (m, 2H), 1.36-1.02 (m, 20K), 0.00 (s, 9H). ¹³C NMR (126 MHz, C₆D₆) δ=69.7, 33.3 (2C), 24.7 (2C), 24.2 (2C), 23.8 (2C), 23.7 (2C), 21.5 (2C), 0.6 (3C). HRMS (EI) exact mass for [M]⁺: calcd m/z 256.2217, found 256.2221.

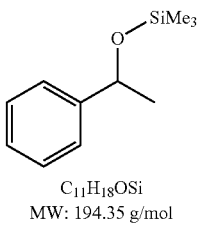

C₁₁H₁₈OSi
MW: 194.35 g/mol

Trimethyl(1-phenylethoxy)silane. Prepared from acetophenone (36.10 mg, 0.30 mmol) and obtained as a colorless oil (59 mg, 99% yield) after 21 h at 110° C. in C₆H₆. IR (ATR): ṽ/cm⁻¹=2957, 1449, 1368, 1249, 1206, 1093, 1031, 956, 834, 748, 696. ¹H NMR (500 MHz, C₆D₆) δ=7.33 (d, J=8.0, 2H), 7.19 (t, J=8.0, 2H), 7.08 (t, J=8.0, 1H), 4.75 (q, J=6.3, 1H), 1.40 (d, J=6.3, 3H), 0.07 (s, 9H). $^{13}$C NMR (126 MHz, C$_6$D$_6$) δ=147.1, 128.5 (2C), 127.2, 125.7 (2C), 71.1, 27.4, 0.2 (3C). HRMS (EI) exact mass for [M]$^+$: calcd m/z 194.1043, found 193.1034.

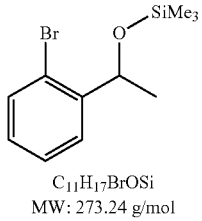

C$_{11}$H$_{17}$BrOSi
MW: 273.24 g/mol (1-(2-Bromophenyl)ethoxy)trimethylsilane. Prepared from 2'-bromoacetophenone (59.70 mg, 0.30 mmol) and obtained as a colorless oil (75 mg, 92% yield) after 15 h at 110° C. in C$_6$H$_6$. IR (ATR): ṽ/cm$^{-1}$=2957, 1369, 1249, 1200, 1093, 1021, 953, 835, 748. $^1$H NMR (500 MHz, C$_6$D$_6$) δ=7.68 (dd, J=7.8, 1.5, 1 H), 7.30 (d, J=7.8, 1 H), 7.00 (t, J=7.8, 1 H), 6.67 (td, J=7.8, 1.5, 1H), 5.35 (q, J=6.2, 1H), 1.43 (d, J=6.2, 3H), 0.06 (s, 9H). $^{13}$C NMR (126 MHz, C$_6$D$_6$) δ=146.2, 132.6, 128.7, 128.4, 127.9, 121.3, 70.0, 25.8, 0.0 (3C). HRMS (EI) exact mass for [M]$^+$: calcd m/z 272.0227, found 272.0227.

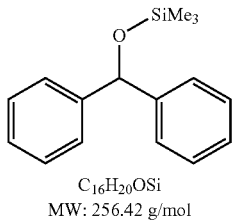 [SMILES: C[Si](C)(C)OC(c1ccccc1)c1ccccc1]

C$_{16}$H$_{20}$OSi
MW: 256.42 g/mol (Benzhydryloxy)trimethylsilane. Prepared from benzophenone (54.70 mg, 0.30 mmol) and obtained as a colorless oil (75 mg, 92% yield) in mixture with trace amounts (<8%) of diphenylmethane after 15 h at 80 ° C. in toluene. IR (ATR): ṽ/cm$^{-1}$=3027, 2955, 1598, 1491, 1451, 1249, 1187, 1060, 880, 833, 735. $^1$H NMR (500 MHz, C$_6$D$_6$) δ=7.38 (d, J=7.5, 4H), 7.13 (t, J=7.5, 4H), 7.03 (t, J =7.5, 2H), 5.73 (s, 1H), 0.06 (s, 9H). $^{13}$C NMR (128 MHz, C$_6$D$_6$) δ=145.5 (2C), 128.5 (4C), 127.3 (2C), 127.0 (40), 77.1, 0.2 (3C). No molecular ion could be detected by high resolution MS.

The invention claimed is:

1. A method for making hydrosilanes having formula R$^1$R$^2$R$^3$SiH (Ia), by reacting a compound having formula I with a Lewis acid of general formulae II or IIa:

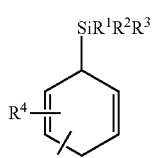

(I)

(II)

(IIa)

wherein
R$^1$ and R$^2$ represent independently from each other C$_1$-C$_3$-alkyl or C$_1$-C$_3$-alkoxy,
R$^3$ represent independently from R$^1$ and R$^2$ H, C$_1$-C$_3$-alkyl, C$_1$-C$_3$-alkoxy or aryl and R$^4$ and R$^5$ represent independently from each other H, C$_1$-C$_3$-alkyl or R$^1$R$^2$R$^3$Si with R$^1$ to R$^3$ as defined above,
R is methyl or ethyl,
m+n=5, m=0 to 5 and n=0 to 5,
with concomitant formation of an arene solvent.

2. The method of claim 1, wherein alkenes of general formula III

(III)

react in solution with the hydrosilanes of general formula Ia

R$^1$R$^2$R$^3$SiH (Ia), with R$^1$ to R$^3$ as above,
to form silanes of general formula IV

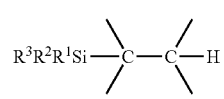

(IV)

with R$^1$ to R$^3$ as above.

3. The method of claim 1 wherein carbonyl compounds of general formula V

(V)

react in solution with the formed hydrosilanes of general formula Ia

R$^1$R$^2$R$^3$SiH (Ia), wherein R$^1$ to R$^3$ have the above meaning,
to form silanes of general formula VI

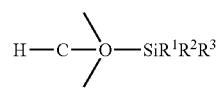

(VI)

with R$^1$ to R$^3$ as above.

4. The method of claim 1, wherein R$^1$, R$^2$ and R$^3$ in formula I are equal to each other representing methyl, ethyl, i-propyl, methoxy or ethoxy.

5. The method of claim 1, wherein R$^1$ and R$^2$ in formula I are equal to each other representing methyl, ethyl, methoxy or ethoxy, and R$^3$ represents H or aryl.

6. The method of claim 1 wherein m in general formula II is 5 and n is 0.

7. The method of claim 1, wherein the reaction is conducted in a solvent at ambient temperature, preferably an arene solvent or a halogenated solvent.

8. The method of claim 1 wherein the reaction is conducted in a solvent at 70-120° C., preferably in an arene solvent or a halogenated solvent.

9. The method of claim 1, wherein the alkenes which are hydrosilylated are alkenes of general formula IIIa

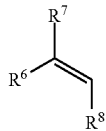
(IIIa)

wherein
$R^6$ represents H, $C_4$-$C_{20}$-alkyl, $C_4$-$C_{20}$-cycloalkyl or aryl,
$R^7$ represents H, $C_1$-$C_{10}$-alky, $C_4$-$C_{10}$-cycloalkyl or aryl, or $R^6$ and $R^7$ form together a cycloalkane ring,
and
$R^8$ represents H, methyl, ethyl, —$CH_2$Hal or phenyl.

10. The method of claim 1, wherein $R^6$ and $R^7$ represent H and $R^8$ represents a —$CH_2$Hal group, preferably —$CH_2$Cl.

11. The method of claim 1, wherein the alkenes which are hydrosilylated are alkenes of general formula III b

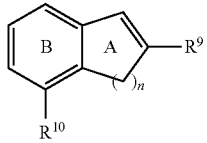
(III b)

wherein
a) in case that both rings A and B are present,
n is 1 or 2,
$R^9$ represents H, $C_1$-$C_{20}$-alkyl or $C_4$-$C_{20}$-cycloalkyl,
$R^{10}$ represents H or halogen;
and
b) in case that ring B is not present,
in the cyclic alkene of ring A n is 1-4 and $R^9$ represents H or methyl.

12. The method of claim 1, wherein the alkene which is hydrosilylated is norbornene (III c).

13. The method of claim 1, wherein the carbonyl compounds which are hydrosilylated are compounds of general formula Va

(Va)

wherein
R represents $C_1$-$C_{20}$ alkyl or aryl,
R' represents H, $C_1$-$C_{20}$ alkyl or aryl or
R and R' form together a $C_3$-$C_{20}$ cycloalkane ring.

14. A method comprising reacting cyclohexa-2,5-dien-1-yl-silanes of general formula (I)

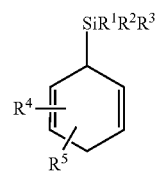
(I)

wherein
$R^1$ and $R^2$ represent independently from each other $C_1$-$C_3$-alkyl or $C_1$-$C_3$-alkoxy,
$R^3$ represent independently from $R^1$ and $R^2$ H, $C_1$-$C_3$-alkyl, $C_1$-$C_3$-alkoxy or aryl and
$R^4$ and $R^5$ represent independently from each other H, $C_1$-$C_3$-alkyl or $R^1R^2R^3$Si with $R^1$ to $R^3$ as defined above,
and a Lewis acid of general formula II or IIa $$B(C_6F_mH_n)_3 \quad (II)$$

wherein m+n=5, m=0 to 5 and n=0 to 5, $$BF_3 \cdot O(R)_2 \quad (IIa)$$

wherein R is methyl or ethyl,
for hydrosilylation of alkenes and carbonyl compounds under concomitant formation of an arene solvent.

* * * * *